Oct. 30, 1951 A. P. HOWARD Plant Pat. 1,047
ROSE PLANT
Filed Sept. 5, 1950
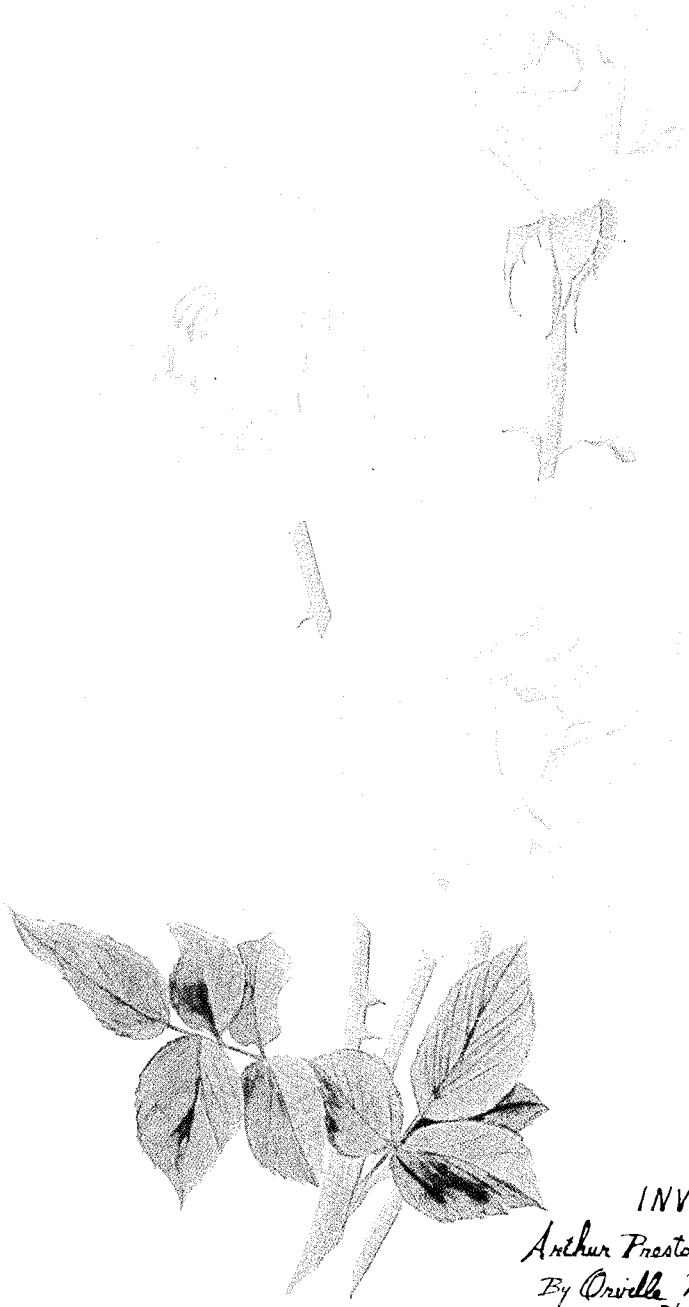
INVENTOR
Arthur Preston Howard
By Orville M. Kile
Plant Pat. Agent.

Patented Oct. 30, 1951

Plant Pat. 1,047

UNITED STATES PATENT OFFICE 1,047

ROSE PLANT

Arthur Preston Howard, Sierra Madre, Calif., assignor to Howard & Smith, Montebello, Calif.

Application September 5, 1950, Serial No. 183,150

1 Claim. (Cl. 47—61)

My present invention relates to a new and useful variety of hybrid tea rose plant of the pink-flowered class. It is the result of a cross made by me in Southern California between Radiance (unpatented) and an unnamed seedling. Its subsequent reproduction by means of budding, in the same general locality, has shown its characteristics to be permanent.

Outstanding among its characteristics are its delicate pink flowers which frequently have a ruffled or fluted appearance, the darker coral tone of the bud, and the prolific production of flowers partially due to the habit of bearing in clusters. Also it is notable that this variety is a strong grower and withstands cold much better than other known varieties having flowers of similar coloring.

The accompanying illustrations shown in as nearly their true form and color as the artist was able to portray them, three specimens of the flower of my new variety in various stages of opening, together with portions of the stems and foliage.

Following is a detailed description of my new variety. Color plate numbers refer to Ridgway's Color Standards and Nomenclature and where no plate numbers are given the ordinary dictionary meaning of the term is intended.

*The plant*

Growth habits:

*Form.*—Spreading bush, attaining a height of 3 to 4 feet.

*Vigor.*—Extremely strong grower.

*Disease resistance.*—Apparently free of mildew, blackspot and other diseases common to roses.

*Cold resistance.*—Hardier than other known varieties of similar coloring.

Stems:

*Color.*—Basic color is approximately Light Cress Green (Pl. XXXI), much of which is overlaid with a bronze or reddish tinge approximating Ocher Red (Pl. XXVII).

*Sturdiness.*—Very strong and heavy.

*Thorns.*—Many; sharp; irregularly placed on stem; outward pointing; large; much the same color as stems.

*Length.*—Main stems very long for a bush rose—2 to 3 feet.

Foliage:

*Type.*—Imparipinnate, usually with 3 to 5 leaflets.

*Size.*—Small to medium. Terminal leaflet of older, larger leaves measures approximately 2¾ inches by 1½ inches. Lateral leaflets are progressively smaller toward stems.

*Quantity.*—Plentiful.

*Shape.*—Oval to elliptical, with acute apex and rounded base. Large leaves and leaflets have considerable inclination to fold at midrib.

*Edge.*—The edge is so finely serrated as to appear entire unless examined closely.

*Texture.*—Heavy and leathery.

*Stipules.*—Prominent; wide; clinging; points acute.

*Color.*—Between Forest Green and Elm Green (Pl. XVII).

*The flower*

Bud:

*Size.*—About 1½ inches long just before unfolding.

*Shape.*—Conical and even.

*Color.*—Approximately Eosine Pink (Pl. I).

*Opening.*—Slow.

*Calyx.*—Small.

*Sepals.*—Mostly simple, with only a few side appendages and only slight tendency to be foliaceous. Reflex early. Usually slightly pink-tinted.

*Peduncle.*—Short and sturdy. Averages 2½ inches long.

Blossom:

*Borne.*—Sometimes the flower is borne singly on long stem and this occurs usually when the plant has been pruned back hard. Mostly, however, flowers are borne in clusters of from 3 to 8, with 4 or 5 open at once in the larger clusters. These clusters usually come on the main stems arising from base of plant and the individual flower stems or peduncles are short.

*Quantity.*—Very floriferous.

*Season.* — Continuous bloomer, March through October in Southern California.

*Form.*—At first the flower has a globular center which often becomes ruffled or fluted after opening. Later the rose flattens, exposing the golden anthers.

*Size.*—Averages 3½ to 4 inches in diameter.

*Petalage.*—About 30 to 35 petals.

*Behavior.*—When cut and put on ice, the petals close and the rose "goes to sleep," opening when removed from icebox.

*Longevity.*—Average.

*Color.*—Outer surface of petals is approximately Hermosa Pink with slight shadings of Eosine Pink. Inner surface is La France Pink. (All three colors Plate I, Ridgway's.)

*Fragrance.*—Tea.

Petals:

*Shape.*—Outer petals almost round, often becoming fluted or wavy on the edges after flower opens. Although the petals are not scalloped, they often appear to be so when the flower is fully open, because of the fluted edges which frequently occur.

*Arrangement.*—Informal.

*Behavior.*—Persistent.

*Size.*—Outer petals are approximately 1¾ inches in each direction, with the inner petals much narrower.

Reproductive organs:

*Pistils.*—Many; bunched in center of flower, partially enclosed in calyx. *Style*—exposed portion short and red-tinged. *Stigma*—small and dull yellow.

*Stamens.* — Many; longer than pistils; bunched about pistils but set at top of calyx; curved inward, partially covering pistils.

*Anthers.*—Golden yellow.

*Filaments.*—Red-tinged.

*Ovary.*—Large; partially enclosed.

Having thus disclosed my invention, I claim:

The new and distinct variety of hybrid tea rose plant, with qualities in combination substantially as herein shown and described, characterized particularly by its strong growth; its prolific production of flowers; its comparative hardiness; its habit of bearing flowers both singly and in clusters; its delicate pink flowers, the petals of which frequently become ruffled or fluted after opening and later flatten to expose anthers; and the habit of its flowers of "going to sleep" when put on ice.

ARTHUR PRESTON HOWARD.

No references cited